United States Patent [19]
Muroff

[11] Patent Number: 5,976,116
[45] Date of Patent: Nov. 2, 1999

[54] MIRRORED EYE DROP TARGET AND METHOD THEREFOR

[76] Inventor: Lenard L. Muroff, 676 Carnation Ct., Wellington, Fla. 33414

[21] Appl. No.: 09/040,975

[22] Filed: Mar. 18, 1998

[51] Int. Cl.[6] .................................................. A61M 35/00
[52] U.S. Cl. .......................... 604/294; 604/295; 604/300
[58] Field of Search ..................................... 604/294, 295, 604/300, 301, 303; 222/212, 419, 420, 421, 422

[56] References Cited

U.S. PATENT DOCUMENTS

| | | | |
|---|---|---|---|
| 3,128,920 | 4/1964 | Volckening et al. | 604/294 |
| 3,913,575 | 10/1975 | Windsor | 604/294 |
| 4,344,430 | 8/1982 | Astove | 604/300 |
| 4,973,322 | 11/1990 | Jewart | 604/300 |
| 5,713,495 | 2/1998 | Menard | 604/300 |

*Primary Examiner*—John G. Weiss
*Assistant Examiner*—David J. Cho
*Attorney, Agent, or Firm*—Robert C. Kain, Jr.

[57] ABSTRACT

The mirrored eye drop target is used in connection with an eye drop container. The drop or dropper target includes an elongated planar substrate having a mirrored or reflective first end segment and an adhering second end segment. In a preferred embodiment, the adhesive on the second end segment is initially covered by a removable substrate or cover. After removal of the substrate (which exposes the adhesive), the planar substrate is attached to the body of the eye drop container. The mirrored or reflective first end segment is substantially vertically aligned with the eye drop spout end such that when the composite structure (the planar substrate and eye drop container) is substantially horizontally disposed, eye drops ejected from the spout end substantially fall in a single vertical line established by the visual target or on the mirrored or reflective surface, the spout end and the user's eye. In other words, when the user visually centers his or her reflected eye image in the target and aligns the image with the spout end, and when the eye dropper is substantially horizontally disposed, fluid falls into the eye upon ejection from the spout end.

15 Claims, 2 Drawing Sheets

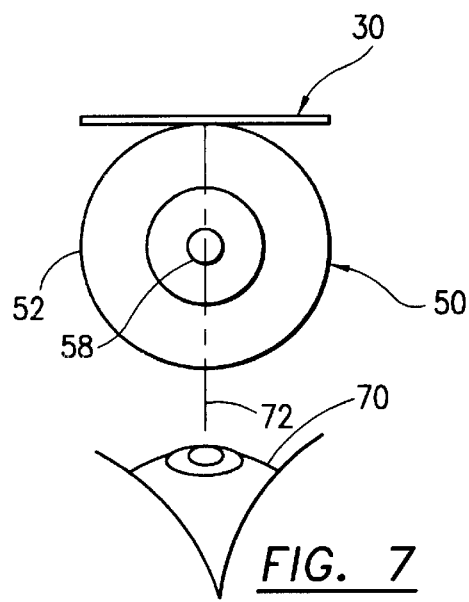
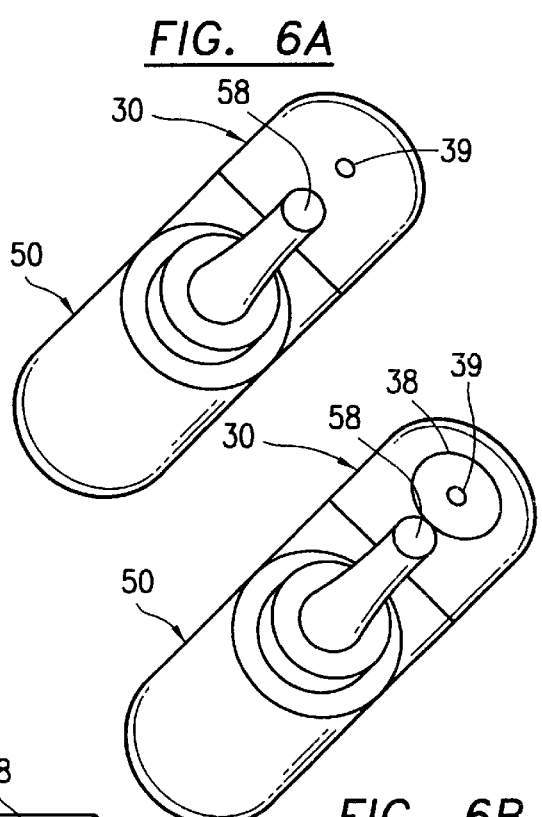
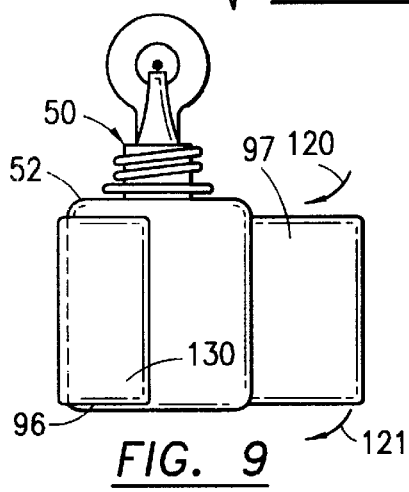
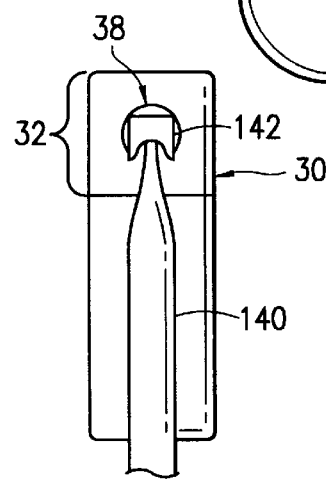
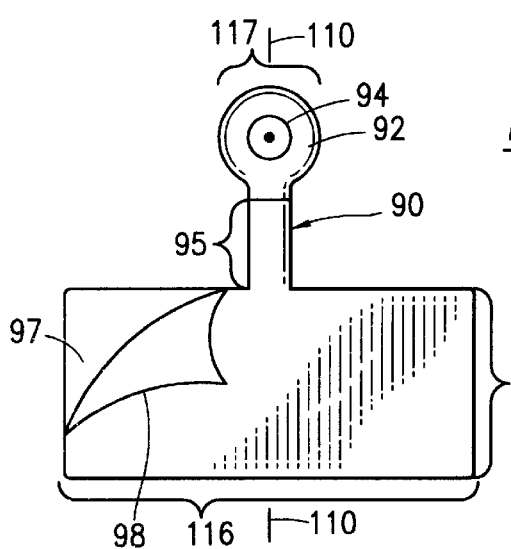
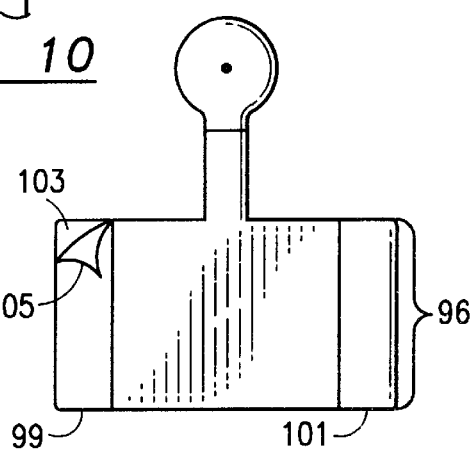

MIRRORED EYE DROP TARGET AND METHOD THEREFOR

BACKGROUND OF THE INVENTION

The present invention relates to a mirrored eye drop target and a method for directing eye drops into an eye of an user.

Eye drops are sometimes utilized by users to deliver medication to the eye or relieve eye strain or simply to clear debris from the eye. Commonly, the eye drops are carried by an eye dropper which normally includes a fluid containment body or container, an eye dropper spout and a spout end. To deliver eye drops into the eye, the user substantially horizontally positions his or her eye and substantially vertically positions the spout end preferably above the pupil of the eye or generally above the eyeball. Hopefully, the user maintains a distance of about 2–4 inches between his or her eyeball and the dropper spout in order to avoid damage to the eye due to inadvertent physical contact. It is relatively difficult to substantially horizontally position the head and eye and substantially vertically deliver the eye drops into the eye cavity and the eyeball. Various structures have been created to accurately position the spout end vertically above the eyeball. U.S. Pat. No. 4,344,430 to Astrove discloses a mirrored surface which is angularly disposed with respect to a substrate. The substrate is angularly attached to the base of the eye dropper. U.S. Pat. No. 3,913,575 to Windsor discloses an eye dropper device which includes a swing out mirror attached to the base of the eye dropper. U.S. Pat. No. 3,779,245 to Windsor discloses another eye dropper which includes a mirrored or reflective surface attached to the base of the eye dropper. All of these systems suffer from the defect that the reflective surface should be in a plane parallel to the axial centerline of the eye dropper and particularly vertically aligned with the eye drop spout and the spout end when the eye dropper is substantially horizontally disposed. The present invention overcomes these difficulties.

OBJECTS OF THE INVENTION

It is an object of the present invention to provide a mirrored eye dropper target and a method for directing eye drops to an eye of an user.

It is an additional object of the present invention to provide an eye dropper target which utilizes an elongated planar substrate having a mirrored first end and an adhering second end such that the planar substrate can be permanently mounted to the eye drop container.

It is an additional object of the present invention to provide a mirrored eye dropper target wherein the user aligns the reflected image of his or her eye with the end of the eye dropper spout such that when the head and eye are in a substantially horizontal position, eye drops, leaving the spout, fall vertically into the eye of the user. Specifically, the user holds the target horizontally over the bridge of his or her nose and pulls down the lower lid of his or her eye with the other hand. This later action exposes a greater eye surface.

It is another object of the present invention to provide a plurality of mirrored eye dropper targets in a "matchbook" or packet form.

It is a further object of the present invention to provide advertising indicia or instructional indicia on the outer cover and, additionally or alternatively on the inside portion of the cover, of the matchbook or packet carrying the plurality of mirrored eye dropper targets.

BRIEF DESCRIPTION OF THE DRAWINGS

Further objects and advantages of the present invention can be found in the detailed description of the preferred embodiments when taken in conjunction with the accompanying drawings in which:

FIGS. 6A and 6B diagrammatically illustrate different visual targets on the reflective or mirrored end segments of the planar substrates when those substrates are mounted on eye drop containers;

FIG. 7 diagrammatically illustrates the substantial vertical alignment of the mirrored or reflective surface, the end of the eye drop spout and the user's eyeball;

FIGS. 8A and 8B diagrammatically illustrate another construction of the planar substrate which includes a wraparound member for the eye drop bottle or container;

FIG. 9 diagrammatically illustrates the partial or full attachment of the wraparound member on the body of the eye drop container; and FIG. 10 diagrammatically illustrates the use of the mirrored eye drop target with a "single" eye drop ampule or container.

SUMMARY OF THE INVENTION

The mirrored eye drop target is used in connection with an eye drop container. The drop or dropper target includes an elongated planar substrate having a mirrored or reflective first end segment and an adhering second end segment. In a preferred embodiment, the adhesive on the second end segment is initially covered by a removable substrate or cover. After removal of the substrate (which exposes the adhesive), the planar substrate is attached to the body of the eye drop container. The mirrored or reflective first end segment is substantially vertically aligned with the eye drop spout end such that when the composite structure (the planar substrate and eye drop container) is substantially horizontally disposed, eye drops ejected from the spout end substantially fall in a single vertical line established by the visual target or on the mirrored or reflective surface, the spout end and the user's eye. In other words, when the user visually centers his or her reflected eye image in the target and aligns the image with the spout end, and when the eye dropper is substantially horizontally disposed, fluid falls into the eye upon ejection from the spout end.

DETAILED DESCRIPTION OF THE PREFERRED EMBODIMENTS

The present invention relates to a mirrored eye drop target and a method of directing eye drops into the eye of a user.

Figure 1:
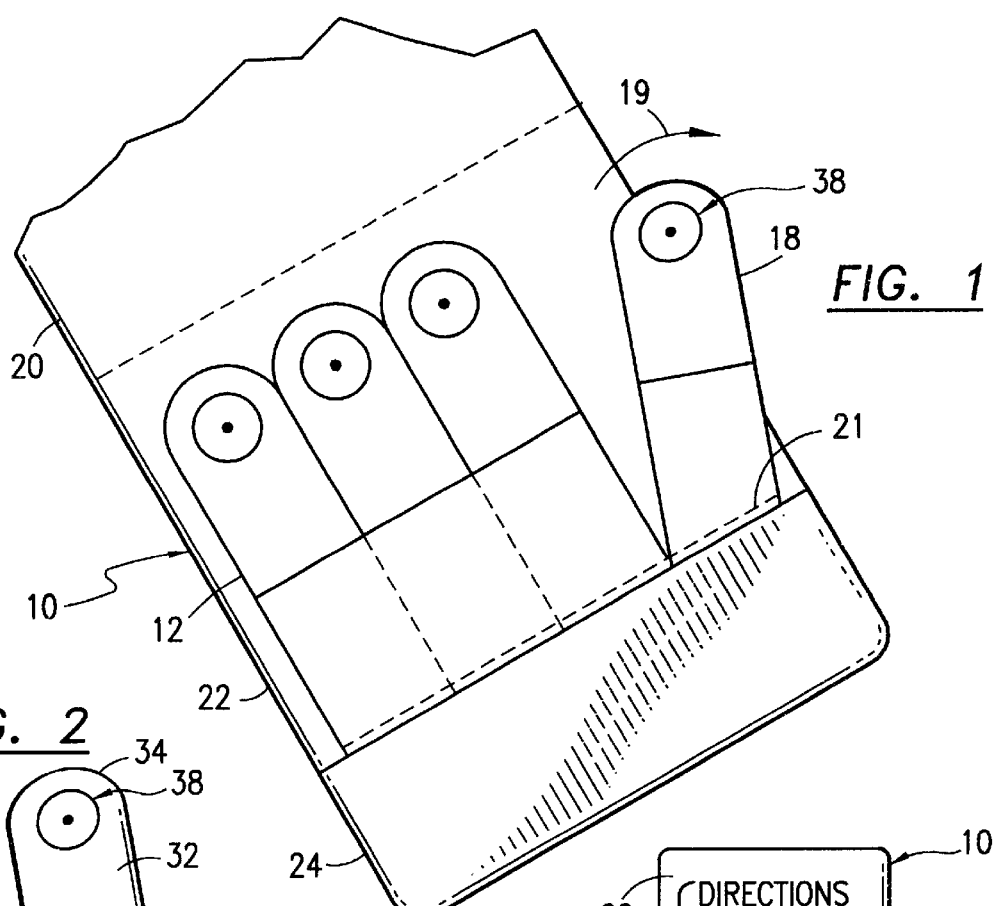
FIG. 1 diagrammatically illustrates a plurality of mirrored eye drop targets in a "matchbook" or packet form.

FIG. 1 diagrammatically illustrates a packet 10 carrying a plurality of mirrored eye drop targets 12, 14, 16 and 18. In the preferred embodiment, packet 10 is shaped generally similar to a matchbook although larger. Other packet configurations may be utilized. Packet 10 includes forward flap 20, rearward flap 22 and wraparound end segment 24. FIG.

Figure 5:
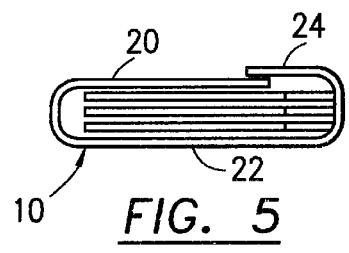
FIG. 5 diagrammatically illustrates vertical stacking of sub-pluralities of eye drop targets.

5 better illustrates the preferred embodiment of the packet. In the preferred embodiment, the distal end of front flap 20 is tucked beneath or inserted beneath the terminal end of wraparound flap 24. Other types of packets may be utilized. Additionally, the packet can be eliminated and the mirrored eye dropper targets may be dispensed individually, or may be dispensed in a sheet form wherein each target is detachably arranged with other targets in a singular plane or the targets may be stacked vertically one atop the other. In these latter embodiments, individual targets may be withdrawn from the group by tearing or cutting. Tearing along a perforated line is preferred. FIG. 5 shows vertical stacking of a plurality of mirrored eye drop targets.

As discussed in detail later, the mirrored eye drop target is configured as an elongated planar substrate. In FIG. 1, drop target 18 has been pulled away from the group of targets in the direction shown by arrow 19. Targets 12, 14 and 16 are horizontally juxtaposed next to each other. These drop targets illustrated in FIG. 1 include perforations or separable indentations 21 near their base which enable the user to easily separate one target from the group or plurality. In one working embodiment, the substrate is rigid cardboard.

Figure 2:
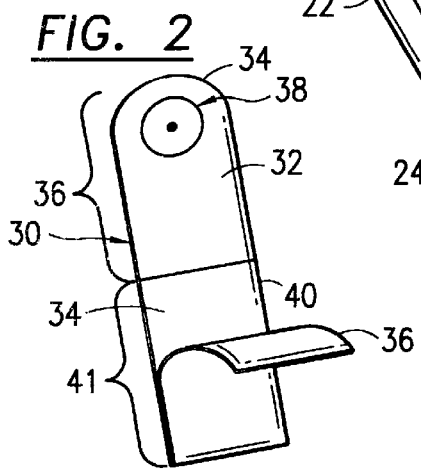
FIG. 2 diagrammatically illustrates a single eye drop target with the protective layer partially removed from the adhering second end segment of the planar substrate.

FIG. 2 illustrates a single eye drop target 30. The major components of drop target 30 include a reflective or mirrored surface 32, an adhesive surface 34, a separable cover 36 and some type of visual target 38 on the reflective or mirrored surface 18. As illustrated in FIGS. 1 and 2, visual target 38 is a "modified bull's eye" which includes a central dot or a small circle at a central location and a larger, concentric circle or marking. A small dot or small circle may be utilized as the sole target on the mirror as shown in FIG. 6A.

The mirrored or reflective surface covers end 34 a distance 36. See FIG. 2. In a preferred embodiment, the balance of the planar substrate 40 spanning distance 41 is covered by an adhesive coating 34. Alternatively, the substrate may include an intermediate section which is not mirrored or covered with adhesive. Preferably, adhesive coating 34 is not exposed to the ambient environment until cover 36 is removed by the user. Removable cover 36 may be a waxed paper or other type of non-stick cover which can be easily removed by the user. Thereafter, the planar substrate is mounted onto the eye dropper container or body via adhering segment surface 34.

Figure 3A:
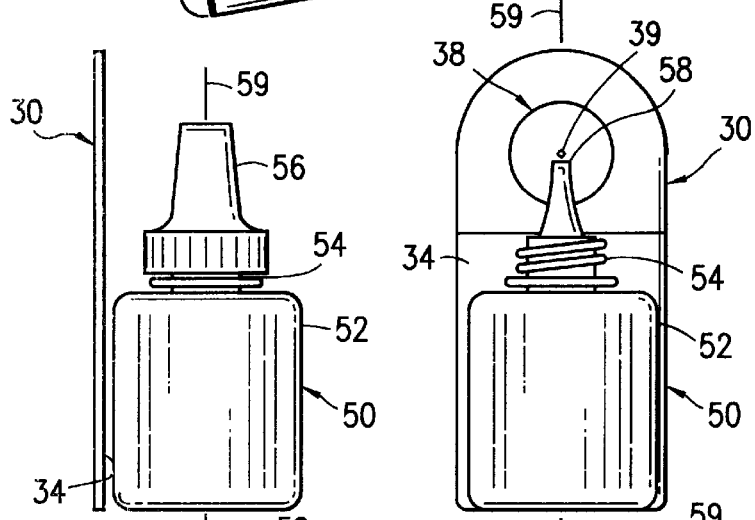
FIGS. 3A and 3B diagrammatically illustrate a side view and a front view of the mirrored eye drop target adhered to an eye drop container.
Figure 3B:
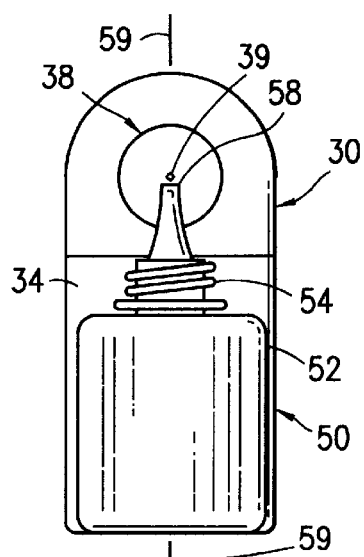

FIGS. 3A and 3B diagrammatically illustrate mirrored eye drop target 30 mounted onto container 50. Container 50 includes a container body 52 and an eye drop spout 54. FIG. 3A illustrates a spout cover 56. FIG. 3B diagrammatically illustrates spout end 58 at the terminal end of spout 54. Container body 52 is elongated as is eye drop spout 54. Axially centerline 59 passes through body 52, eye drop spout 54 and spout end 58.

In operation, the user peels off cover 36 from mirrored eye drop target 30 and places the target and particularly the adhesive covered segment 34 onto body 52. The placement of the mirrored eye drop target must be aligned such that spout end 28 is aligned with target site 38 and particularly central dot or small circle 39.

FIGS. 6A and 6B diagrammatically illustrate perspective views of eye dropper container 50 with mounted drop targets 30. The alignment of spout end 58 with inner target marking or indicia 39 is diagrammatically illustrated.

FIG. 7 diagrammatically illustrates the use of the mirrored eye drop target. In use, the user substantially horizontally orients the composite structure consisting of eye dropper container 50 and mirrored eye drop target 30 and substantially vertically places eye drop spout 58 above his or her eye 70. In order to achieve vertical alignment, the user visually confirms that his or her reflected eye image is aligned in the target (see target 38 in FIG. 3B). Upon alignment and visual centering of the reflected eye image in the target, the user squeezes or depresses eye dropper body 52 thereby ejecting one or more drops of fluid from spout end 58. Since the spout end is vertically aligned with the target 38 (FIG. 3B) when the composite structure is substantially horizontally oriented, when the user aligns his or her reflected eye image in the target, drops from spout end 28 will fall downward in the direction of vertical line 72 into eye 70 of the user. This operation and alignment is diagrammatically illustrated in FIG. 7.

As clearly shown in FIG. 7 and FIG. 3A, the mirrored eye drop target is in a single plane which is parallel to the axial center line of body 52 and eye drop spout 54. Further, the planar substrate carrying the reflective or mirrored surface is spaced apart from eye drop spout 54 and spout end 58. As such, the mirrored surface is cantilevered from body 52 by the adhering end segment. Further, planar substrate or dropper target 30 is always maintained in a singular plane and that plane is always tangential to the periphery of body 52 of eye dropper container 50.

Figure 4:
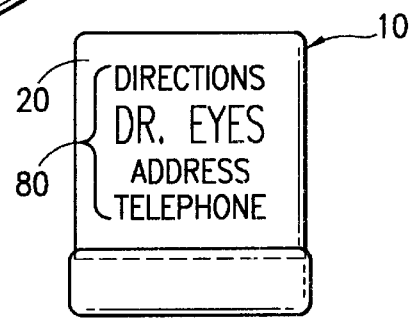
FIG. 4 diagrammatically illustrates the matchbook or packet form of the plurality of mirrored eye drop targets carrying advertising and instructional indicia.

FIGS. 4 and 5 diagrammatically illustrate other embodiments of the present invention. In FIG. 4, advertising indicia 80 and instructional indicia are printed on front packet face 20. Additionally, instructions for use of the mirrored eye drop target and/or medical instructions may be imprinted on the front flap 20 of packet 10. Alternatively, the indicia may be imprinted on the backside of flap 22 or on the inside of the flap.

FIG. 5 diagrammatically illustrates that the mirrored eye drop targets may be stacked vertically in packet 10. The present invention encompasses a system wherein a plurality of mirrored eye drop targets is stacked vertically above another plurality of horizontally juxtaposed targets. FIG. 1 shows a plurality of horizontally juxtaposed targets. Multiple vertical stacks of horizontally disposed eye drop targets may be prepared for other health care providers and/or users.

FIGS. 8A and 8B diagrammatically illustrate a different configuration for mirrored eye drop target 90. In the embodiment illustrated in FIGS. 8A and 8B, mirrored target 90 includes a reflective or mirrored end 92 carrying a visual target 94, an intermediate section 95 and an adhering section 96. Adhering section 96, in the embodiment illustrated in FIG. 8A, includes an adhesive coating 97 and a removable protective shield 98.

In FIG. 8B, adhering segment 96 includes two sub-segments 99 and 101. Adhesive composition 103 covers adhering sections 99, 101. In order to expose adhesive 103, the user removes protective cover or layer 105. The protective cover has not been removed from adhering section 101. In both the figures, the elongated planar substrate 90 includes an axially center line 110 passing through reflective or mirrored end segment 92 as well as adhering segment 96. However, the width 116 of adhering section 96 (normal to axial centerline 110) is much larger than the width 117 of reflective end surface 92.

FIG. 9 diagrammatically illustrates adhering segments 96 being wrapped, either partially or fully, around body 52 of eye dropper container 50. The wraparound occurs as shown by arrows 120, 121. Adhesive surface 97 (or adhesive surface 103 in the embodiment of FIG. 8A) is carried by wraparound body 52 and either attaches to the body itself or attaches to the exposed side 130 of adhesive segment 96. In a further enhancement, adhering segment 96 may be a transparent substrate such that when wrapped around body 52, the instructions or warning on the body are visible to the user. Further, the entire substrate, other than the mirrored segment may be transparent plastic.

FIG. 10 diagrammatically illustrates the use of a mirrored eye drop target 30 with a single or very small eye dropper container or ampule 140. Ampule 140 may deliver 1–10 eye drops to the user. The user opens ampule 140 by twisting end 142 and removing it. The ampule must be stored upright. Accordingly, reflective end surface 32 and target 38 is fully exposed and cantilevered from the body of the ampule thereby enabling the user to easily deliver eye drops to his or her eye simply by substantially horizontally disposing the target and eye dropper, visually centering his or her reflected eye image in the target and squeezing ampule body 140. Alternatively, the ampule may carry eye ointment which is dropped into the eye as described above with respect to eye drops.

The claims appended hereto are meant to cover modifications and changes within the scope and spirit of the present invention. The mirrored segment may have different shapes than those illustrated herein. The use of the term "eye drop container" is meant to cover a fluid carrying container and an ointment carrying container. This construction is possible because in a general sense, ointment flows and forms drops similar to eye drop liquid.

What is claimed is:

1. A mirrored eye dropper target for use with an eye drop container having a body and an eye drop spout at one end of said body, said eye drop spout designed to deliver drops to an eye of a user, said target comprising:

an elongated planar substrate having a mirrored first end segment and an adhering second end segment, said adhering second end segment having a covered mode wherein an adhesive coating on said planar substrate is not exposed to an ambient environment and an adhering mode wherein said adhesive coating physically attaches said planar substrate to said body; and said mirrored first end segment carrying a visual target thereon for alignment of the eye drop spout over said eye of said user.

2. A mirrored eye dropper target as claimed in claim 1 wherein said visual target is a central dot or small circle.

3. A mirrored eye dropper target as claimed in claim 1 wherein said visual target is a modified bull's eye.

4. A mirrored eye dropper target as claimed in claim 1 wherein in said adhering mode, said mirrored end segment is cantilevered in a singular plane over said eye drop spout and said visual target is substantially vertically aligned with a distal end of said eye dropper spout when said planar substrate and attached container are horizontally oriented.

5. A mirrored eye dropper target as claimed in claim 4 wherein said visual target is one from the group consisting of a central dot, small circle and a modified bull's eye.

6. A mirrored eye dropper target as claimed in claim 1 wherein said body is elongated and has an outer peripheral dimension, said elongated body being coaxial with said eye drop spout, and said planar substrate is elongated and has an axial centerline passing through said first and second end segments and said adhering second end segment has a width, normal to said axial centerline, sufficient to wraparound a portion of said periphery of said body.

7. A mirrored eye dropper target as claimed in claim 5 wherein said body is elongated and has an outer peripheral dimension, said body being coaxial with said eye drop spout, and said planar substrate is elongated and has an axial centerline passing through said first and second end segments and said adhering second end segment has a width, normal to said axial centerline, sufficient to wraparound a portion of said periphery of said body.

8. A packet of mirrored eye dropper targets, each target utilized in connection with an eye drop container having a body and an eye drop spout at one end of said body, said eye drop spout designed to deliver drops to an eye of a user, said packet of targets comprising:

a packet having an outer packet cover with an end cover segment adapted to be bent over to be adjacent an opposite cover end of said packet;

a plurality of elongated planar substrates juxtaposed near each other inside said packet;

each elongated planar substrate having a mirrored first end segment and an adhering second end segment, said adhering second end segment having a covered mode wherein an adhesive coating on said planar substrate is not exposed to an ambient environment and an adhering mode wherein said adhesive coating physically attaches said planar substrate to said body; and each said mirrored first end segment carrying a visual target thereon for alignment of the eye drop spout over said eye of said user.

9. A packet of mirrored eye dropper targets as claimed in claim 8 wherein each of said elongated planar substrates is juxtaposed horizontally.

10. A packet of mirrored eye dropper targets as claimed in claim 8 including a first and a second sub-plurality of elongated planar substrates, each planar substrate in a respective sub-plurality being juxtaposed horizontally with respect to other planar substrates in the same sub-plurality, said second sub-plurality of planar substrates being juxtaposed vertically with respect to said first sub-plurality of planar substrates.

11. A packet of mirrored eye dropper targets as claimed in claim 8 wherein said visual target is one from the group consisting of a central dot, small circle and a modified bull's eye.

12. A packet of mirrored eye dropper targets as claimed in claim 11 wherein in said adhering mode, said mirrored end segment is cantilevered in a singular plane over said eye drop spout and said visual target is substantially vertically aligned with a distal end of said eye dropper spout when said planar substrate and attached container are horizontally oriented.

13. A packet of mirrored eye dropper targets as claimed in claim 11 wherein said body is elongated and has an outer peripheral dimension, said elongated body being coaxial with said eye drop spout, and said planar substrate is elongated and has an axial centerline passing through said first and second end segments and said adhering second end segment has a width, normal to said axial centerline, sufficient to wraparound a portion of said periphery of said elongated body.

14. A packet of mirrored eye dropper targets as claimed in claim 13 including one of advertising indicia and instructional indicia printed on said outer packet cover.

15. A plurality of mirrored eye dropper targets as claimed in claim 8 including one of advertising indicia and instructional indicia printed on said outer packet cover.

* * * * *

UNITED STATES PATENT AND TRADEMARK OFFICE
CERTIFICATE OF CORRECTION

PATENT NO. : 5,976,116
DATED : November 2, 1999
INVENTOR(S) : Lenard L. Muroff

It is certified that error appears in the above-identified patent and that said Letters Patent is hereby corrected as shown below:

In the drawings, sheet 2: FIG. 8A (second occurrence on right hand side) should be changed to --FIG. 8B--.

Signed and Sealed this

First Day of May, 2001

Attest:

NICHOLAS P. GODICI

Attesting Officer     Acting Director of the United States Patent and Trademark Office